United States Patent [19]
Brunderman

[11] Patent Number: 6,142,156
[45] Date of Patent: *Nov. 7, 2000

[54] FOOTCARE DEVICE AND METHOD OF USING SAME

[76] Inventor: Pamela Jean Brunderman, Seven Lake St., #8J, White Plains, N.Y. 10603

[ * ] Notice: This patent is subject to a terminal disclaimer.

[21] Appl. No.: 09/324,331

[22] Filed: Jun. 2, 1999

Related U.S. Application Data

[63] Continuation of application No. 09/184,772, Nov. 2, 1998, Pat. No. 5,913,313.
[60] Provisional application No. 60/064,078, Nov. 3, 1997.

[51] Int. Cl.⁷ .................................................. H45D 29/04
[52] U.S. Cl. ........................................ 132/76.4; 132/200
[58] Field of Search ......................... 132/76.4, 73, 76.2, 132/200; 451/523, 494, 524, 557, 525; D28/63; D4/137

[56] References Cited

U.S. PATENT DOCUMENTS

| | | | |
|---|---|---|---|
| D. 326,931 | 6/1992 | Tomsick | D28/63 |
| D. 343,476 | 1/1994 | Tomsick | D28/63 |
| 1,495,445 | 5/1924 | Salm | 132/76.4 |
| 3,196,885 | 7/1965 | Emmerson | 132/76.4 |
| 3,900,976 | 8/1975 | Kitts, Jr. | 451/494 |
| 4,246,914 | 1/1981 | Keyser | 132/76.4 |
| 4,520,525 | 6/1985 | Yogi et al. | 15/104.92 |
| 5,758,381 | 6/1998 | Rocha | 15/160 |
| 5,813,416 | 9/1998 | Rudolph | 132/76.4 |
| 5,816,266 | 10/1998 | Cone | 132/76.4 |

FOREIGN PATENT DOCUMENTS

| | | |
|---|---|---|
| 9301942 | 11/1993 | Netherlands . |
| 2280849 | 2/1995 | United Kingdom . |
| 9524175 | 9/1995 | WIPO . |

*Primary Examiner*—Pedro Philogene
*Attorney, Agent, or Firm*—Cummings & Lockwood

[57] ABSTRACT

Footcare products and methods for caring for human feet useful for removing calluses, corns and the like from human feet while the human is standing on a surface, such as, a shower floor and applying an abrasive surface to the human foot is disclosed. Representative devices for at least partially alleviating foot discomfort due to skin build-up, such as, calluses include a base structure having an upper and a bottom surface, connecting means, operatively connected to the bottom surface of the base structure, for removably connecting the base structure to a solid surface, and abrasive structure operatively connected to the upper surface of the base structure, for removing skin build up from a human foot. Methods for using the footcare device are also disclosed.

20 Claims, 9 Drawing Sheets

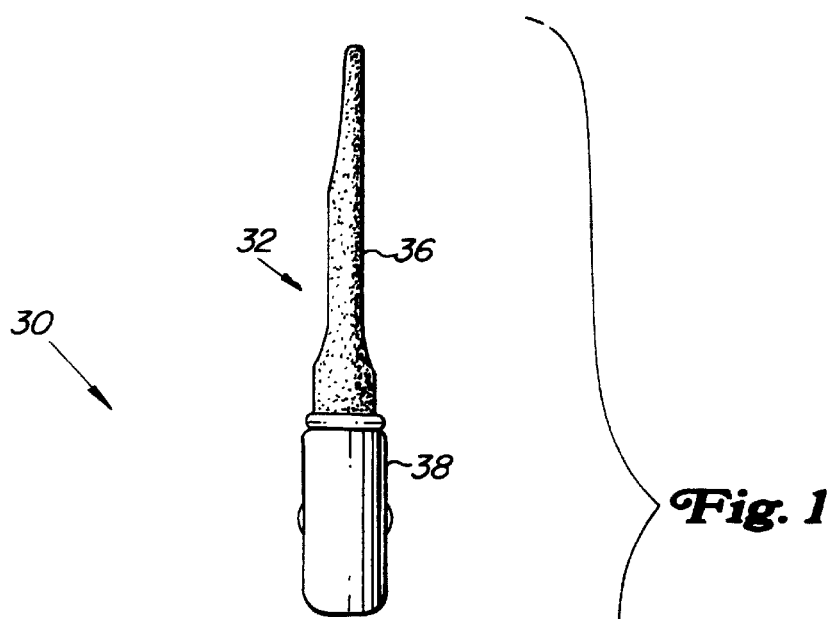
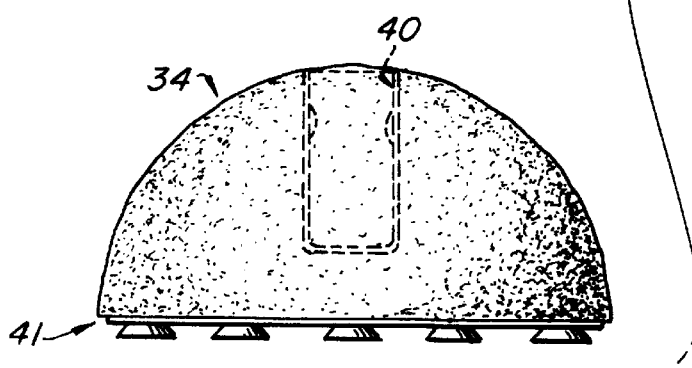
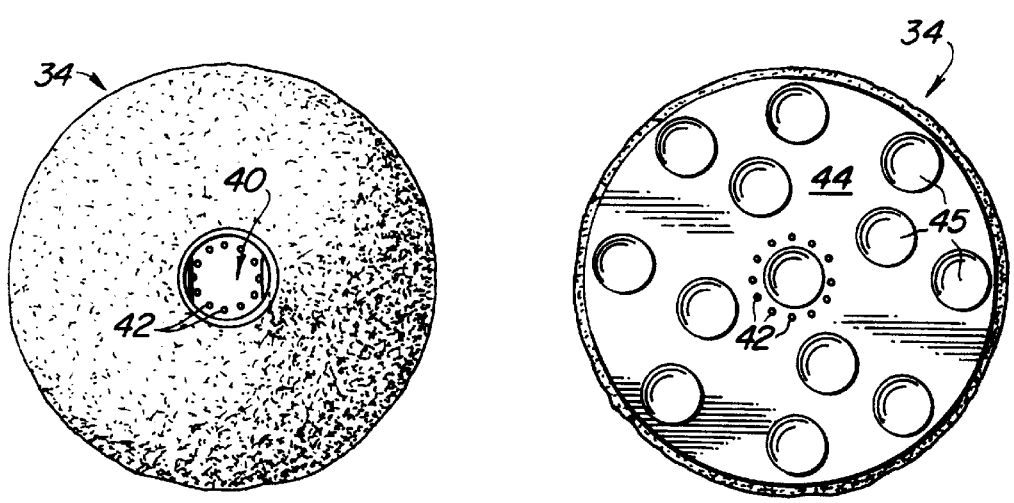
Fig. 2    Fig. 3

FOOTCARE DEVICE AND METHOD OF USING SAME

RELATED APPLICATIONS

This application is a continuation of Ser. No. 09/184,772 filed Nov. 2, 1998, U.S. Pat. No. 5,913,313 and also claims the benefit of U.S. Provisional Patent Application Ser. No. 60/064,078, filed Nov. 3, 1997, of Brunderman, the disclosure of which is herein incorporated by reference.

BACKGROUND OF THE INVENTION

The present application relates generally to footcare products and methods for caring for human feet. More specifically, it relates to footcare products and methods for removing calluses, corns and the like from human feet. Most specifically, it relates to stationary footcare products and methods for removing calluses, corns and the like from human feet while the human is standing on a surface, such as, a shower floor and applying an abrasive surface to the human foot.

It is known that skin built upon the foot such as calluses and corns are a recurring problem to human feet having been subjected to prolonged friction and pressure. Currently available treatments such as medicated pads and other devices for the removal of such hardenings of skin have been found not to provide prompt or adequate relief to the feet.

One particular prior art design for removing dead skin, calluses and other formations from the foot and stimulate its blood circulation is described in U.S. Pat. No. 4,246,914 to Keyser. This particular patent discloses an elongated bar having an abraded surface and a smooth surface. In use, the bar is placed horizontally, e.g., on the floor, vis-a-vis the seated user, who places his right foot firmly and supportively on the smooth surface of the bar so that the bar will remain stationary on the floor. The user then draws his left foot across the abraded surface which when drawn with adequately applied pedal pressure across the abraded surface, relieves calluses, corns, dead skin, etc. developed under the foot sole.

While this prior art device was successful in providing some relief for sufferers of foot calluses and corns, using such device has proven difficult or inconvenient for use in the daily routine of an active person. Specifically, the subject device and other currently available treatments for such calluses, etc. such as, for example, a pumice stone have all proven to be difficult to use in the shower. The abrasive textures has worked well but the convenience of the application to the foot has been considerably inadequate.

Usually, the manufacturers of such products recommend that they be applied to the feet when the feet are wet. Clearly, the quickest and easiest way for a human to obtain wet feet is in the shower or tub along with perhaps soaking the feet in a foot tub. Using the hand applied products of the prior art, standing in the shower on one foot to apply the devices to the other foot was unsafe. Utilization of a tub soak required more time and effort than the average busy person would be willing to invest.

Thus, there is a need for devices and methods for caring for human feet which would allow a human to stand safely in a shower or tub or on another surface while applying an abrasive to the various areas of the feet to remove the dead skin, calluses, corns, etc. as well as to stimulate the blood circulation in the foot. Such devices and methods should work passively and safely to help maintain the human foot by removing dead skin, calluses and corns, etc.

Such devices and methods should smooth the rough skin on the bottom, top, sides and/or in between the toes of the feet. Such devices and methods should reduce calluses and provide general foot maintenance. Such devices and methods should produce a massaging effect to the feet when they are rubbed on this device. Such devices and methods should have non-allergenic properties. Such devices and methods should be operated passively, and "hands-free" by the user. Such devices and methods should assist in the alleviation of foot discomfort due to skin build-up and calluses.

SUMMARY OF THE INVENTION

It is one object of the present invention to provide devices and methods for smoothing the rough skin on the bottom, top, sides and in between the toes of the feet.

It is another object of the present invention to provide devices and methods which reduce calluses and provides general foot maintenance.

It is yet another object of the present invention to provide devices and methods which produces a massaging effect to the feet when they are rubbed on this device.

It is still another object of the present invention to provide devices and methods that has non-allergenic properties.

It is another object of the present invention to provide devices and methods that are resistant to mildew.

It is another object of the present invention to provide devices and methods that are operated passively, and "hands-free" by the user.

It is yet another object of the present invention to provide devices and methods which increase the safety and comfort of a user during use.

It is still another object of the present invention to provide a device which aids and assists in the alleviation of foot discomfort due to skin build-up and calluses.

It is another object of the present invention to provide devices and methods for caring for human feet safety in a shower or tub while standing.

In accordance with these and further objects, one aspect of the present application includes a device for at least partially alleviating foot discomfort due to skin build-up, such as, calluses, the device comprising: a base structure having an upper and a bottom surface; connecting means, operatively connected to the bottom surface of the base structure, for removably connecting the base structure to a solid surface; and abrasive means, operatively connected to the upper surface of the base structure, for removing skin build up from a human foot.

Yet another aspect of the present application includes a method for removing skin from a human foot, the method comprising the steps of: providing a device for at least partially alleviating foot discomfort due to skin build-up, such as, calluses, the device including: a base structure having an upper and a bottom surface; connecting means, operatively connected to the bottom surface of the base structure, for removably connecting the base structure to a solid surface; and abrasive means, operatively connected to the upper surface of the base structure, for removing skin build up from a human foot; operatively positioning the device at a desired location on a flat surface; applying pressure from a point on top of the device to activate the connecting feature of the device, thereby securing the device in the desired location; wet and lather the foot with a thin layer of soap and water so that the foot can glide easily over the rough texture of the device; and moving the foot over the outer surface of the device in at least one of a plurality of possible motions while applying slight pressure with the foot.

Other objects and advantages of the application will be apparent from the following description, the accompanying drawings and the appended claims.

BRIEF DESCRIPTION OF THE DRAWINGS

FIG. 1 is an elevation view of a first representative embodiment of one possible two-piece footcare device of the present invention.

FIG. 2 is a plan view of a representative pumice rubbing mound base component of the embodiment of FIG. 1;

FIG. 3 is a plan view of suction cup base positioned on the bottom of the rubbing mound base of FIG. 2;

FIG. 16B is an elevational/side view of the embodiment of the footcare device of FIG. 16a;

DETAILED DESCRIPTION

Figure 4:
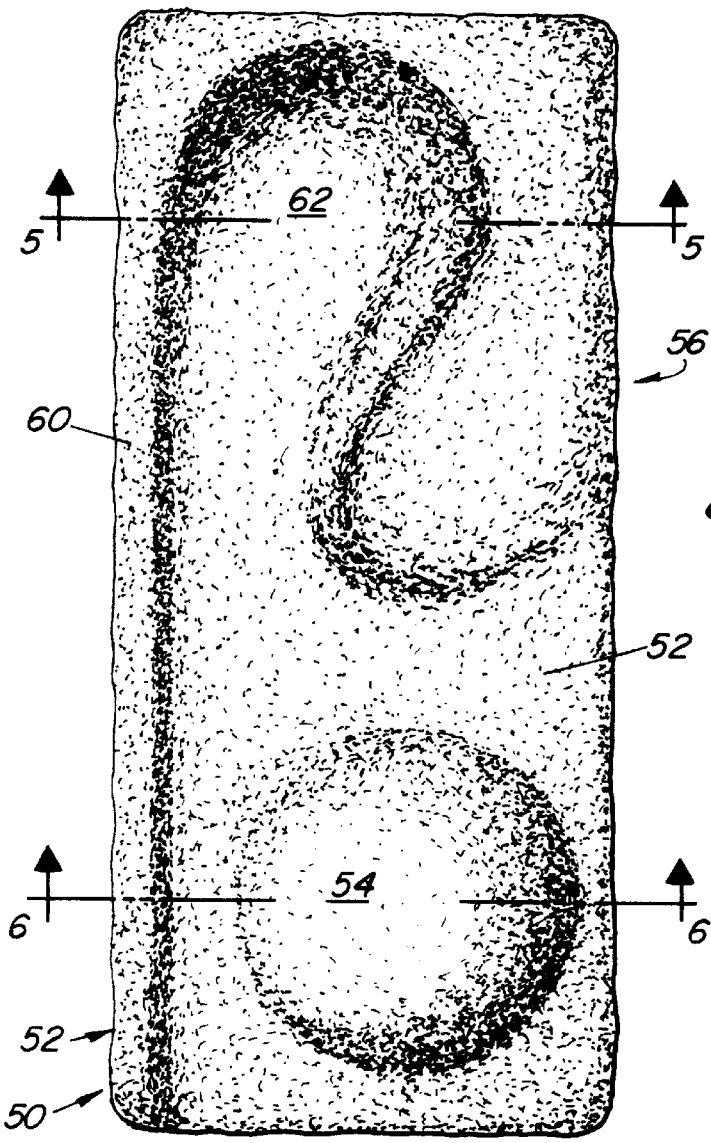
FIG. 4 is a plan view of a representative embodiment of a one-piece footcare device.
Figure 5:
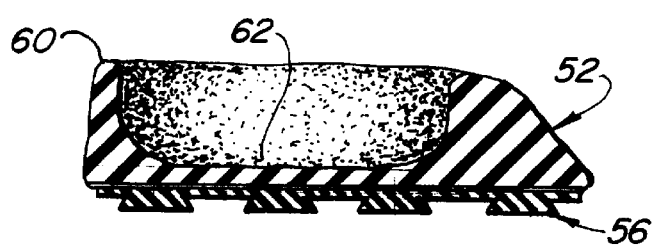
FIG. 5 is a sectional view along line 5—5, of the foot care device of FIG. 4.
Figure 6:
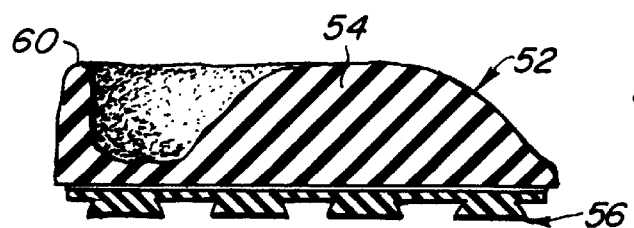
FIG. 6 is a sectional view taken along line 6—6, of the embodiment of FIG. 4.
Figure 7:
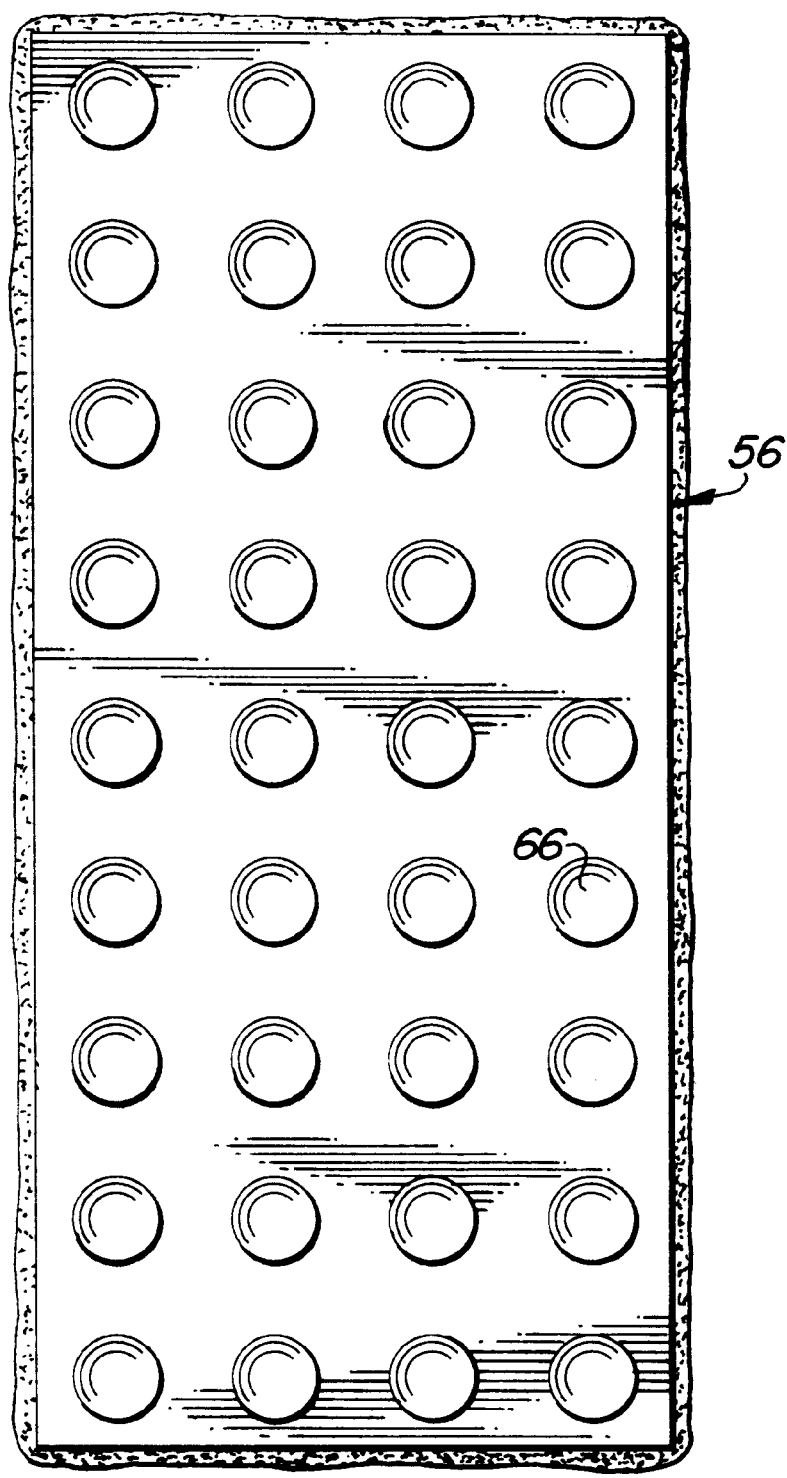
FIG. 7 is a plan view of the suction cup base connected to the bottom of the one-piece footcare device of FIG. 4.

The present invention is a footcare device useful for the exfoliation of the flaking top layer of skin on the foot, the exfoliation and reduction of calluses on the foot and for general footcare maintenance. These exfoliations become necessary when the skin build-up or callus produces pain and/or discomfort while wearing shoes, walking, preparing for sleep and other normal everyday activities. It is believed that many people suffer from the effects of this skin build-up and therefore normal and daily activities performed are done so with, in some cases, at least some discomfort. The present invention is designed to assist in the alleviation of this discomfort.

FIGS. 1–3 illustrate a first representative embodiment of the present invention, a pumice skin smoother footcare device 30. The footcare device 30 comprises two working parts, a contoured abrasive toe stick 32, and a rubbing mound 34.

The toe stick 32 is, presently preferably, about 4 5/8" long by 5/8" round at its widest point and 1/4" wide at its narrowest point and is comprised of two sections. The first section otherwise referred to as the contoured abrasive section 36, is designed to be used for the areas in between and around the toes of the foot for the purpose of exfoliation of the flaking top layer of skin and callus build-up in these areas. Its shape is, presently preferably, comparable to that of the shape of one particular representative device, #47593-51, called, Contoured File commercially available for Dr. Scholl®.

Additionally, the texture of the contoured abrasive section 36 is, presently preferably, comparable to the texture of the contoured file available from Dr. Scholl®, as mentioned above. The second section, otherwise referred to as the contoured smooth section 38, of the contoured abrasive toe stick 32, is designed as a functional attachment intended to be operatively connected to the rubbing mound 34. The second section, 38 is preferred that when the contoured abrasive toe stick 32 is operatively positioned in the cavity 40 of the rubbing mound base component 34, that the top surface of the rubbing mound base component 34 aligns with the point at which the contoured abrasive section 36, and the contoured smooth section 38 of the contoured abrasive toe stick 32 meet.

The rubbing mound 34 of the first representative embodiment of the present invention, a pumice skin smoother footcare device 30 as shown in FIGS. 1–3 is, presently preferably, sized about 6" round by 2 3/16" high with a flat bottom 42, and includes five features.

The first feature of the rubbing mound 34 is the texture, which is comparable to such as, for example, the device called, "Natural Pumice Stick," distributed by L'Esprit, a division of Sunny Marketing Systems, Inc., Port Washington, N.Y.

The second feature of the rubbing mound 34 is the cavity 40 positioned at the top center of the rubbing mound 34, which is specially designed to operatively receive the smooth contoured section 38 of the contoured abrasive toe stick 32. Attachment of the contoured abrasive toe stick 32 in the cavity 40 may be by use of a friction fit or other such retaining device or mechanism. The cavity 40 presently preferably, comprises a hole having about a ¾" diameter by about 1 ½" deep.

The third feature of the rubbing mound 34 is a connecting means, such as, for example, a suction cup 44 made by Rubbermaid® for securing the device 10 to a flat surface, such as, for example, a tub or shower stall floor during use.

The fourth feature of the rubbing mound 34 is a conventional adhesive means sufficiently adhesive to operatively retain the connection therebetween.

The fifth feature of the rubbing mound 34 is a drain means, presently preferably, a plurality of drain holes 42, presently preferably, sized at about ⅟₃₂" in diameter. The drain holes 42 are about evenly spaced at the bottom of the cavity 40 for providing passage of water or liquid to escape the cavity 40. The drain holes 42 extend down through the suction cup base 44, and should be sufficient to allow for the drainage of water that may accumulate in the cavity 40.

Assembly Procedures

Having described one representation the footcare device 30, the device is assembled as follows. First, the user inserts the contoured smooth section 38 of the contoured abrasive toe stick 32 into the receiving/connecting cavity 40 of the rubbing mound 34, so that the point at which the smooth and abrasive textures of the contoured abrasive toe stick 32 meet is level with the top of the rubbing mound 34. The contoured abrasive toe stick 32 is locked into place by means of a friction fit or other such connecting device.

Method of Use

Now that the assembly procedure has been completed, next, the method of using the device will be described. First, after having assembled the device, the user moistens the retaining means, such as, for example, the plurality of suction cups 45 of the suction cup base 44 with water. The user then positions the rubbing mound 34 at a desired location on a flat surface, such as, for example, that of the floor of a tub or shower stall. Next, the user applies slight pressure from a point on top of the rubbing mound 34 to activate the suction feature of the suction cup base 44, thereby securing the rubbing mound 34 in place. At this point, the rubbing mound 34 is ready for use and can be used with or without the insertion of the contoured abrasive toe stick 32.

Next, the user simply wets and lathers the foot with a thin layer of soap and water which is intended to act as a lubricant, thereby allowing the foot to glide easily over the rough texture of the rubbing mound 34. The user moves the foot over the surface of the rubbing mound 34 in a backward and forward motion, a side to side motion, or a rotating motion while applying slight pressure with the foot, focusing particular attention to the areas of the foot with callus build-up. It is suggested that the user experiment with the various rubbing motions to determine which motion is the most comfortable.

Another method of use of the present invention, the pumice skin smoother footcare device 30, as shown in FIGS. 1–3, will now be described. The user assembles the contoured abrasive toe stick 32 and the rubbing mound 34 as described above. Once toe stick 32 and the rubbing mound 34, are assembled and the footcare device 30 is secured in place as described above, begin again by lubricating the foot with a thin layer of soap and water.

The user glides the contoured abrasive section 36 of the contoured abrasive toe stick 32 in between the desired toes to be rubbed. The user would gently squeeze the toes thereby applying positive pressure so as to "grip" the contoured abrasive toe stick 32 with the toes, and rub in an upward and downward motion. The user would repeat as necessary to maintain general foot wellness and eliminate the build-up of calluses and flaking skin.

It is presently believed that the total time per foot should take about one to about two minutes with a frequency of approximately four to five times per week. But, more or less may be appropriate for each individual user. It is recommended that this practice be repeated during daily shower or bath to gently, safely and gradually reduce and eliminate flaking surface skin and calluses from the foot.

Upon completion of use of the present invention, the pumice skin smoother device 30 for feet, it is suggested that the device 10 be removed from the tub or shower stall floor by simply breaking the seal of the suction cup base or other such attachment device. It is presently believed that it is best to remove the footcare device 30 daily rather than leaving it in place due to the potential safety risk of tripping or falling over it in the tub or shower stall.

Second Representative Embodiment

A second representative embodiment of the present invention, as shown in FIGS. 4–7, comprises a pumice footcare device 50. The pumice footcare device 50 is, presently preferably, about 4" wide by 9" long by 1 ³⁄₁₆" high and includes two functioning components: the contoured abrasive foot pad 52, and the suction cup base 56.

The first functioning component, or a contoured abrasive foot pad 52, is of a texture comparable to that of a device called, "Natural Pumice Stick," distributed by L'Esprit, a division of Sunny Marketing Systems, Inc., Port Washington, N.Y. The contoured abrasive foot pad 52 is specially designed and shaped, and comprises three features.

The first feature is a toe ridge 60 and is, presently preferably, about 7" long by ¾" high and is sufficiently wide to allow the user to straddle the toe ridge 60 with the toes of the foot while gently squeezing the toes, thereby applying positive pressure so as to "grip" the toe ridge 60 with the toes. Move the foot in a backward and forward motion thereby exfoliating the skin in between the toes of the feet.

The second feature of the contoured abrasive foot pad 52 is a rubbing mound 54 and is, presently preferably, about 2 ¾" round by 1" high at its highest point and slopes down at a degree of about 40°. The foot pad 52 is designed to allow the user to freely rub various parts of the foot on the surface of the rubbing mound 54 in a backward and forward, side-to-side or rotating motion.

The third feature of the contoured abrasive foot pad 52 is a heel cup 62 and is, presently preferably, sized to allow the heel of an average, above average and below average sized adult to comfortably fit in the heel cup 62 so as to be able to rotate the foot in a side-to-side motion while keeping the heel of the foot in place in the heel cup 62. It is presently envisioned that the second representative embodiment of the present invention, the pumice footcare device 50, be sized according to a range of shoe sizes.

The second functional component of the second representative embodiment of the present invention, the pumice footcare device 50 for feet is a connecting means, such as, for example, a suction cup base 56, an example of which of an acceptable means is made by Rubbermaid®, for securing the device to the tub or shower stall floor during use. The suction cup base 56 is attached to the underside of the contoured abrasive foot pad 62 by means of an adhesive or other conventional means sufficient to operatively retain the connection therebetween.

Having described the second representative embodiment, the method of using the second representative embodiment will now be described. A user first moistens the suction cups 66 of suction cup base 56 with water. Next, the user positions the footcare device 50 at desired location on floor of tub or shower stall. The user applies slight pressure from a point on top-center of the contoured abrasive footpad 52 to activate the suction feature of the suction cup base 56, thereby securing the footcare device 50 in place. At this point, the contoured abrasive footpad 52 is ready for use.

Next, the user would simply lubricate the foot with a thin layer of soap and water, thereby allowing the foot to glide easily over the rough texture of the contoured abrasive footpad 52. The user would move the foot over the surface of the toe ridge 60, the rubbing mound 54 and the heel cup 62 in motions described above, while applying slight pressure. The user would vary the pressure applied while rubbing in response to skin sensitivity and personal comfort. It is recommended that the user experiment with various rubbing techniques to determine what is best for the particular user. The user should re-lubricate the foot during rubbing as necessary. The user should repeat the above steps as necessary to maintain general foot wellness and eliminate the build-up of calluses and flaking skin.

It is presently believed that the total time per foot should take about one to about two minutes with a frequency of approximately four to five times per week, but more or less may be appropriate for each individual user. It is recommended that this practice be repeated during daily shower or bath to gently, safely and gradually reduce and eliminate flaking surface skin and calluses from the feet.

Upon completion of use of the second representative embodiment of the present invention, a pumice footcare smoother device 50 for feet, it is suggested that the device 50 be removed from its position on the tub or shower stall floor by simply breaking the seal of the suction cup base 68 or other such attachment device. It is believed that it is best to remove the footcare device 50 daily rather than leaving it in place due to the potential safety risk of tripping or falling over it in the tub or shower.

Figure 8A:
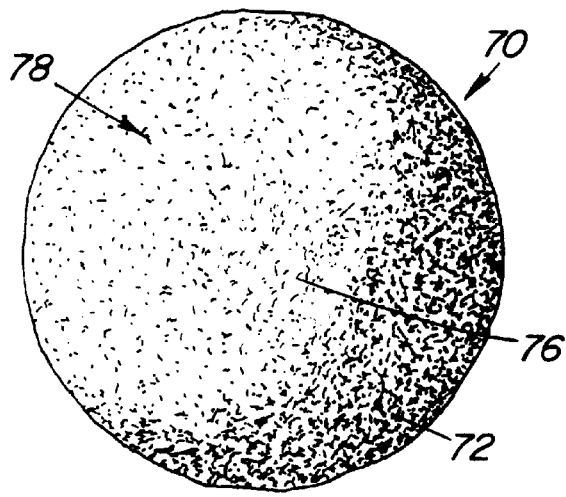
FIG. 8A is a plan/top view of one presently preferred embodiment of the present invention.
Figure 8B:
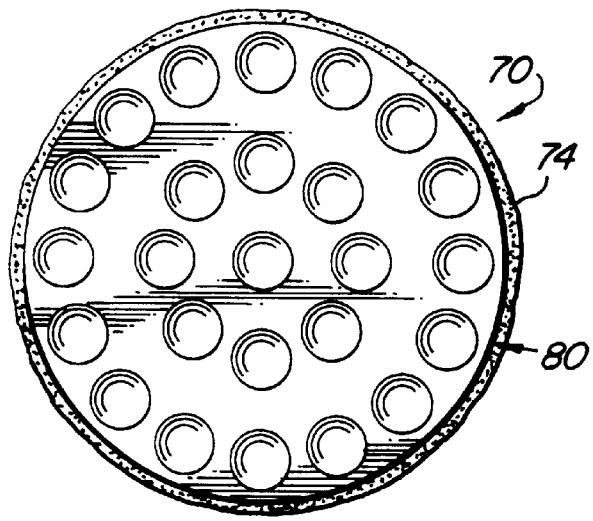
FIG. 8B is a plan/bottom view of the presently preferred embodiment of FIG. 8A.
Figure 8C:
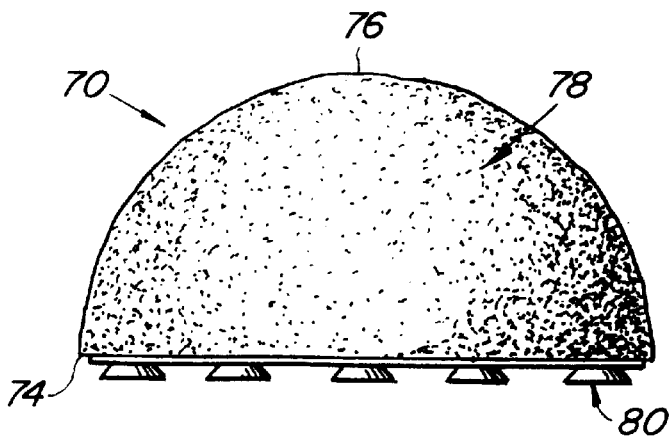
FIG. 8C is a side elevation view of the presently preferred embodiment of FIGS. 8A and 8B.

The presently preferred embodiment of the present application is illustrated in FIGS. 8A–8C. As shown, the footcare device 70 comprises a circular base structural member 72 having a flat broad bottom portion 74 and a curved upper surface 76. The outer surface 78 of the upper portion comprises various abrasive materials which will be discussed later. The bottom portion 74 includes a plurality of suction cups 80 operatively connected to the bottom portion 74 of the base structural member 72. This particular embodiment is similar to the embodiments of FIGS. 1 and 3 with the exception that the cavity and drainage holes, as well as the contoured abrasive post stick of the embodiment of FIGS. 1–3 have been eliminated.

Figure 9A:
FIG. 9A is a side view of the presently preferred embodiment of a connecting device useful for removably connecting the device of the present application to a solid surface.
Figure 9B:
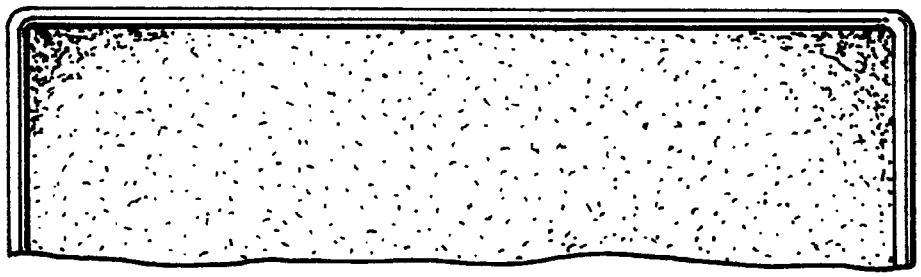
FIG. 9B is a top view of the presently preferred connecting device before its application to the device of the present application before its attachment to the base structure portion of the device of a present application.
Figure 9C:
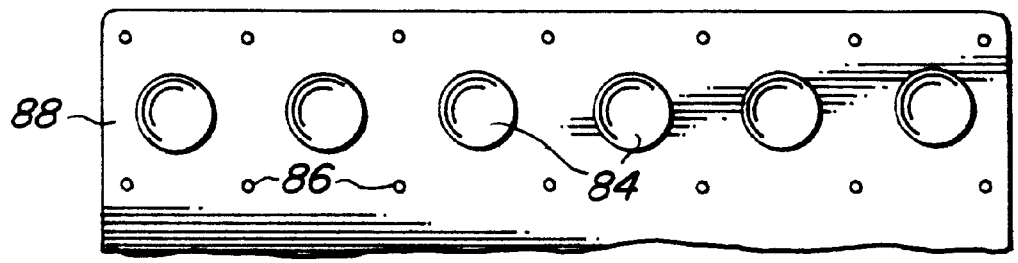
FIG. 9C is a bottom view of the presently preferred connecting device useful with the device of the present application.

FIGS. 9A–9C illustrate the presently preferred connecting device 82 which is operatively connected to the structural base member 72 and which is then used to connect to a solid surface such as a shower stall floor or a tub or a bathroom floor. This particular device has suction cups 84 and gripper fingers 86 alternately positioned on the bottom surface 88 thereof, or the surface which contacts the solid surface. The preferred connecting device 82 is illustrated in FIGS. 9A and 9B prior to being applied to the bottom surface of a base structural member.

Other Representative Embodiments

In each of the following alternative embodiments, the solid surface connecting device is not shown. However, it should be understood that the preferred connecting device of FIGS. 9A–C is presently preferably used to connect each alternative embodiment to the solid surface.

Figure 10A:
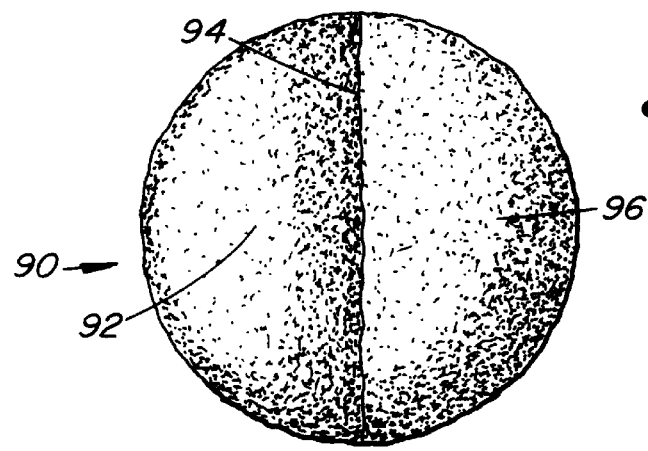
FIG. 10A is a plan/top view of another alternative footcare device of the present application.
Figure 10B:
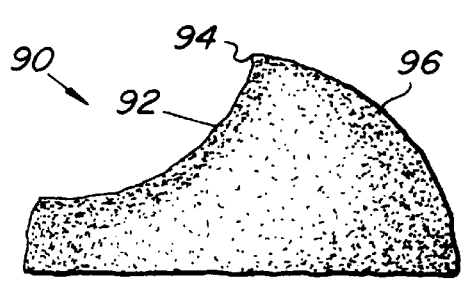
FIG. 10B is an elevation/side view of the alternative footcare device of FIG. 10A.
Figure 10C:
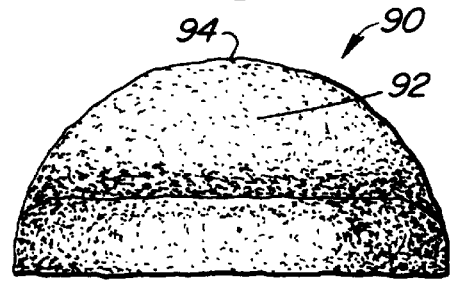
FIG. 10C is an elevational view of the footcare device of FIG. 10A.

FIGS. 10A–10C illustrate yet another alternative embodiment of the footcare device 90 of the present application. This device 90 is similar to that of FIGS. 8A–8C, except that one portion of the upper surface of the structural device has a concave surface 92 as shown in FIG. 10B as opposed to semi-circular side profile of FIG. 8C. When using device 90, the ridge 94 formed at the juncture of the concave 92 and the convex 96 surface is used to remove the skin or calluses between the toes, the convex surface is used for treatment of the arch of a foot, and the concave surface 92 is used for treatment of the heel and sides of the foot.

Figure 11A:
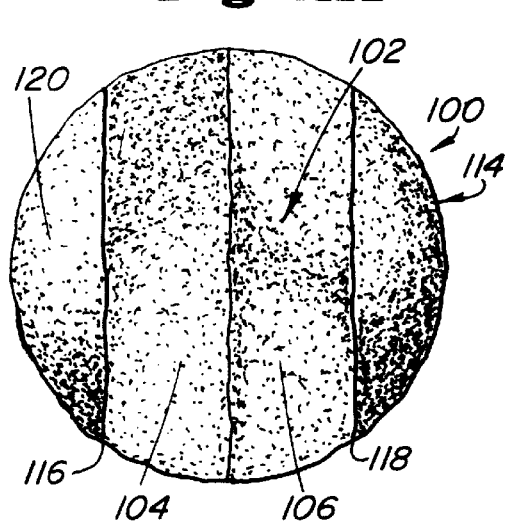
FIG. 11A is a plan/top view of still another alternative footcare device in accordance with the present application.
Figure 11B:
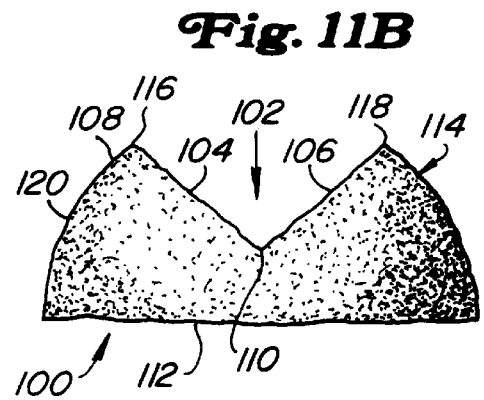
FIG. 11B is an elevation view of the footcare device of FIG. 11A.

FIGS. 11A and 11B illustrate a yet further alternative embodiment 100 of the present invention is shown. As illustrated, the generally semi-circular side elevation of the device of FIG. 8C is modified by essentially forming a trough 102 therein. The trough 102 has two sides 104, 106 which move inwardly from the outer surface 108 of the side elevation until they intersect 110 near the center, leaving a sufficient distance between the intersection point 110 and the bottom surface 112 of the structural base member 114. As shown, the linear surfaces are used to remove the skin buildups on the heels, sides and bottom of the feet, the two ridges 116, 118 formed at the intersection of the circular outer radius of the structural device and the intersection of the trough 102 on both sides is used for in between the toes, with the outer surface 120 of the circumference of the semi-circular portion that remains being used on the arch of the foot.

Figure 12A:
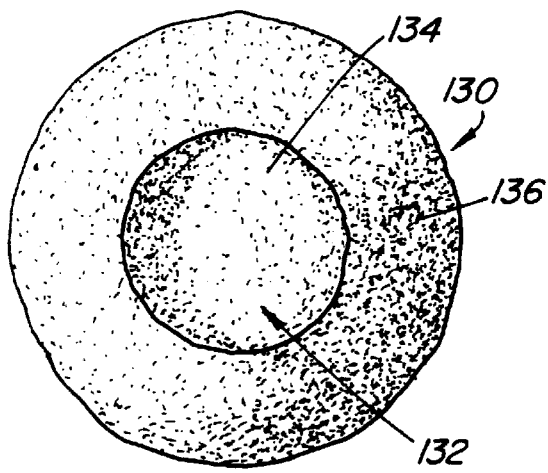
FIG. 12A is a plan/top view of another embodiment of a footcare device in accordance with the present application.
Figure 12B:
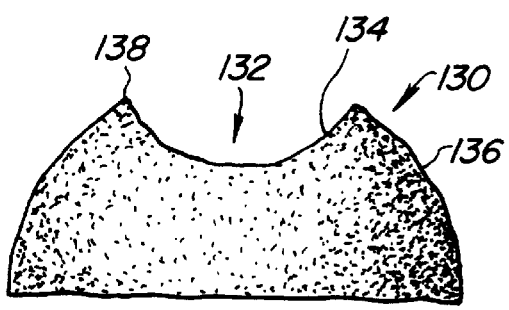
FIG. 12B is an elevation/side view of the alternative footcare device of FIG. 12A.

FIGS. 12A and 12B illustrate yet another representative alternative embodiment 130. As shown in FIG. 12B, a portion 132 of the outer surface of the semi-circular version similar to that of FIG. 8A has been cut away so that a semi-circular concave surface 134 has replaced the upper portion of the convex area of FIG. 8A. In use, this convex area or "Divot" is used to rub the heel and remove skin therefrom, while the arch and ball of the foot and side of the foot is rubbed against the outer surface 136 of the removal of the semi-circular cross section. The ridge 138 formed at the intersection of the circular portion is used for removing skin between the toes.

Figure 13A:
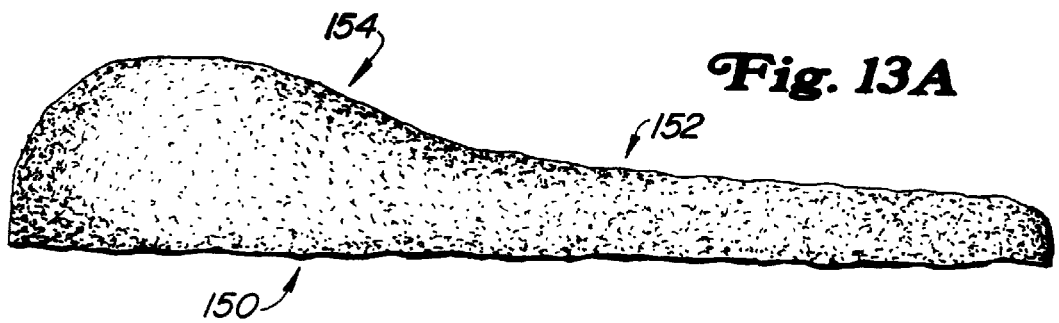
FIG. 13A is an elevational/side view of still another alternative footcare device in accordance with the present application.
Figure 13B:
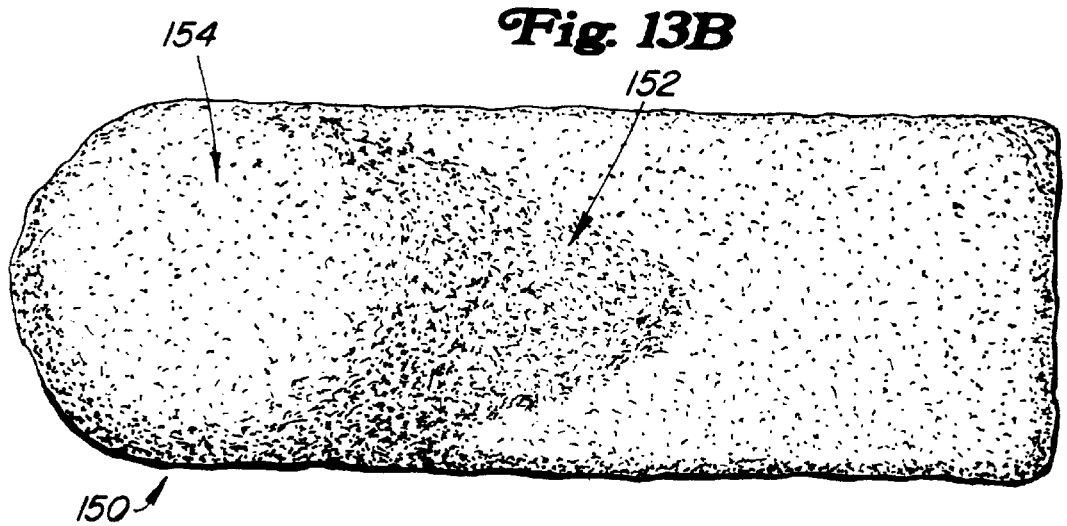
FIG. 13B is a plan/top view of the footcare device of FIG. 13A.

FIGS. 13A and 13B illustrate still another alternative embodiment, or "the slope" version, of the footcare device 150 of the present application. This particular device 150 includes an elongated portion 152 and a mound portion 154 that are operatively connected and flow naturally. This particular device 150 can be used to remove excess skin from all areas of the bottom and sides of the feet. However, there is no provision for rubbing the abrasive surfaces between the toes.

Figure 14A:
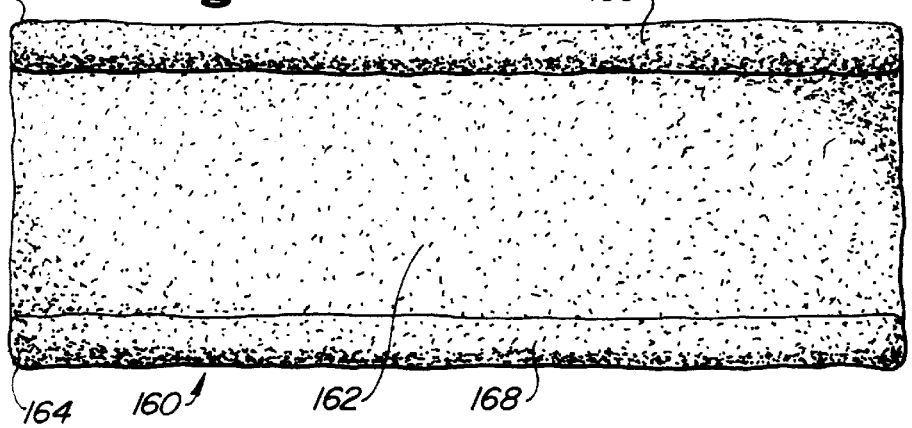
FIG. 14A is a plan/top view of yet another alternative footcare device of the present application.
Figure 14B:
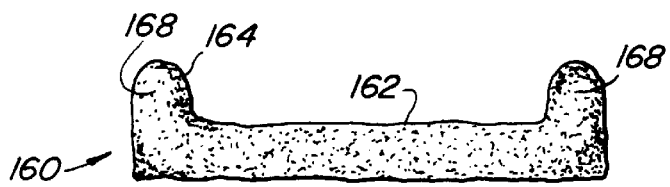
FIG. 14B is an end view of the footcare device of FIG. 14A.

FIGS. 14A and 14B illustrate another alternative footcare device 160 known as "the canyon" version of the present application. As illustrated, the device 160 is essentially rectangular in shape having a flat portion 162 connecting two ridges 164, 166, with each ridge having a semi-circular top 168, 170. The flat portion 162 between the two ridges 164, 166 is utilized to remove the skin buildup on the underside of the foot. The portions of the ridges 164, 166 contiguous with the flat portion 162 are used for the side of the feet with the outer portion of the two ridges 164, 166 also being used for the side of the feet. Each of the two ridges are used for removing excess skin from between the toes.

Figure 15A:
FIG. 15A is a sectional view taken along line 15A—15A of FIG. 15B.
Figure 15B:
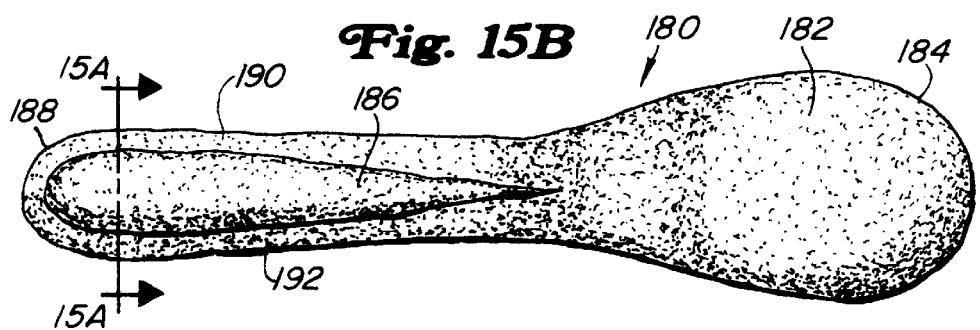
FIG. 15B is a plan/top view of the alternative footcare device.
Figure 15C:
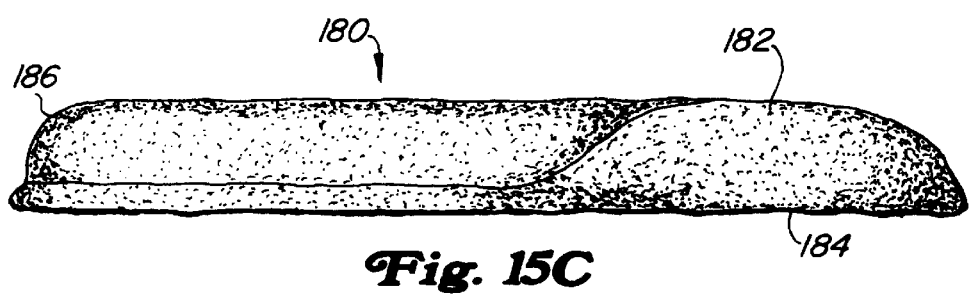
FIG. 15C is an elevational/side view of the alternative footcare device.

FIGS. 15A–15C represent still another alternative embodiment of the footcare device 180 or "spoon version" of the present application. As shown, the device 180 is elongated, having a mound 182 at one end 184 and a trough area 186 at the other 188. The mound 182 at one end is used for the underside of the foot and the arches, with the ridges 190, 192 found around the trough area 194 being used for in between the toes of the feet when removing excess skin.

Figure 16C:
FIG. 16C is a sectional view taken along line 16C—16C of FIG. 16A.
Figure 16A:
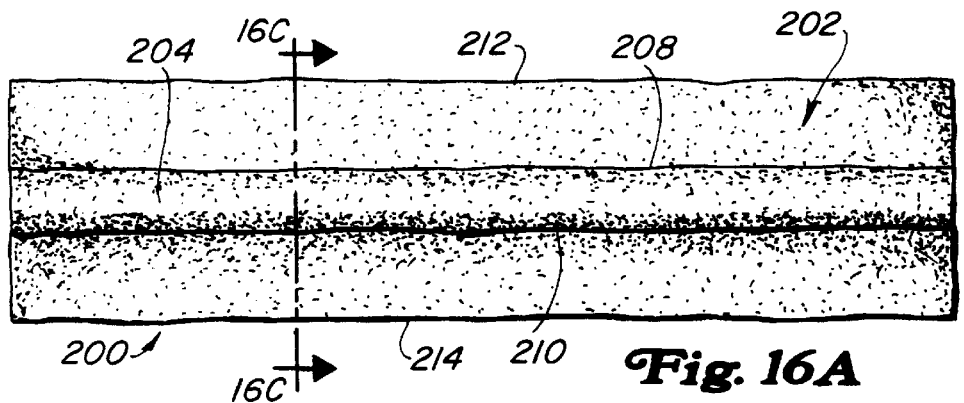
FIG. 16A is a plan/top view of still another alternative embodiment of the footcare product device of the present application.
Figure 16B:
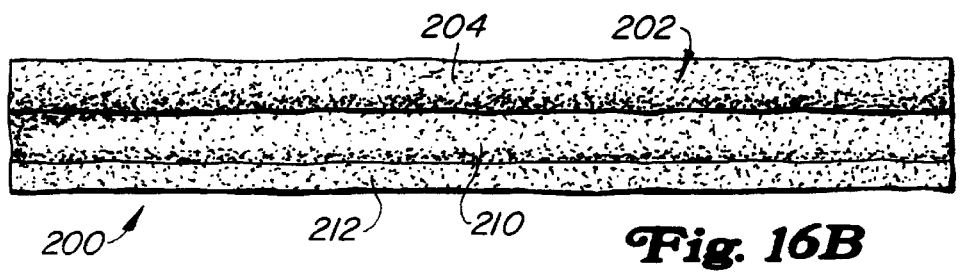

FIGS. 16A–16C illustrate still another alternative embodiment of the footcare device 200 or the "beaded molding" version of the present application. The embodiment 200 includes an elongated portion 202 having a ridge 204 formed approximately in the middle thereof and connected to an essentially circular ridge 206 in the middle portion thereof and having approximately arcuate sides 208, 210 from the middle ridge 204 to each of the side boundaries 212, 214. When using this particular device 200, the person would use the ridge portion 206 primarily for in between the toes and the entire underside of the foot while each of the sloping areas 208, 210 connecting the ridge 204 to the outer sides would be used for the side, big toes and heels of the foot.

Figure 17:
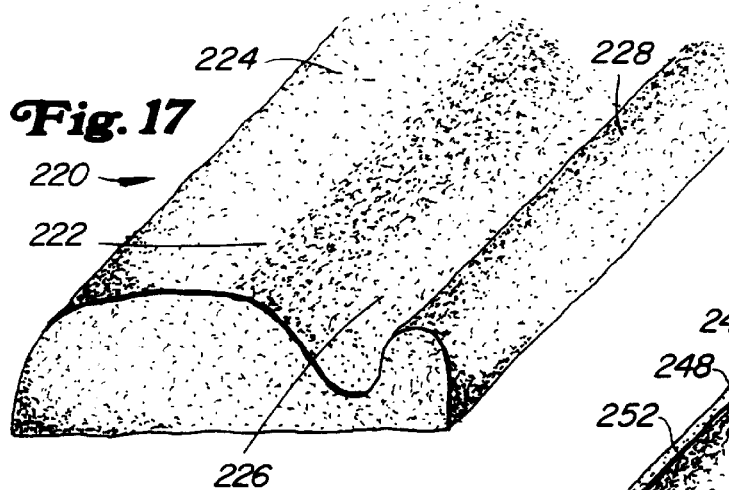
FIG. 17 is a perspective view of still another alternative embodiment of the footcare device of the present application.

FIG. 17 illustrates an even further alternative embodiment of the footcare device 220 of the present application, or the "hill and valley" version. As shown, an elongated structural member 222 includes an arcuate portion or rubbing mound 224, a valley portion 226 and a ridge portion 228. The rubbing mound 224 is utilized to remove excess skin from the underside of the foot, the arch, the ball of the foot, the heel and the bottom of the toes. The ridge portion 228 is used to remove excess skin from between the toes.

Figure 18:
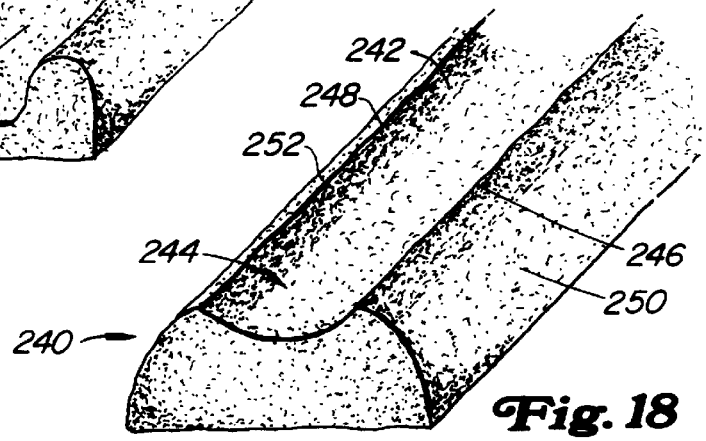
FIG. 18 is a perspective view of another alternative embodiment of the footcare device of the present application.

FIG. 18 represents one last possible alternative embodiment of a footcare device 240 of the present application or "the elongated divot" version. As illustrated, an elongated structural member 242 has a gully 244 formed lengthwise therein. As illustrated, the gully 244 is utilized with the heel of the foot to remove excess skin from the heel of the foot and the ridges 246, 248 formed by the gully 244 with the two sides of the elongated device is used to remove excess skin from between the toes. The side surfaces or the outer surfaces 250, 252 of the portion between each side of the gully 244 and the curved side of the structural member is used for the arch of the foot as well as the entire underside of the foot.

While we have described quite a number of possible embodiments of the footcare device of the present application, it is believed that a considerable number of other such devices could be imagined and implemented and this application is intended to encompass all such possible embodiments.

It should be pointed out the preferred connecting device for connecting the footcare device with the solid surface, such as, for example, a shower floor or a tub, is a combination of a plurality of suction cups and a plurality of gripper fingers. While it is presently believed that the plurality of suction cups without the gripper fingers would work, it is presently preferred that the connecting means include a plurality of suction cups and a plurality of gripper fingers. Concerning the size of the suction cups, it is presently preferred that the plurality of suction cups be about one-half inch in diameter. It is believed to be possible to use suction cups anywhere from three quarters of an inch to two inches in diameter. Further, it is believed possible to utilize individual suction cups and operatively connect them to the bottom of a structural member individually using an appropriate adhesive.

Another possible way of removably securing the footcare device to the solid surface is by what is known as a grip liner, commercially available from Rubbermaid®, Wooster, Ohio. Typically, the grip liner, a trademark device, which resists slipping, would be operatively connected to the bottom of a structural base member by an adhesive or the like. While it may be feasible to use such devices as the grip liner by Rubbermaid®, such devices have not been tested and are not known at this point to be operative.

Concerning the individual suction cups which might be used in this particular type application are available from Suction Cups, Inc., 225 Baker Street, Greenport, N.Y. 11222.

Concerning the abrasive material which would be on the outer surface of the structural member and which would be in contact with the skin of the foot, the structural member itself could be made of many abrasive materials, such as, for example, concrete, silica or glass stone, ground pumice or volcanic rock. Other possible materials would be sand and Styrofoam.

There are a tremendous number of materials which might be available which would accomplish the required function of removing the skin in a comfortable, safe manner include terra cotta foaming pumice, as distributed by Abbaco, Inc., material used in a personal pumi bar which is commercially available from Teregen Labs Pharmaceuticals, P.O. Box 5025 Wilowick, Ohio 34095, a pumice sponge, believed to be made out of polyethylene, available from Titania of Germany, as Article No. 3,000, ceramic, which is available as a ceramic callous remover made by Excellent and sold by Brookstone; a material used in a "two-sided" foot scrubber; available at the Bath and Body Works; clay, also available as a two-sided foot scrubber by Bath and Body Works; and a material used in a foot filesold under the Dr. Scholl® label as a contoured file.

There are also a tremendous number of materials which might be available which would accomplish the required function of connecting the device to the solid surface, such as, for example, the shower floor. The "Grip Liner" by Rubbermaid has already been discussed. Also a "Bath Mat" product by Rubbermaid, #7041 may also be used. Another possible connecting device is "Vinyl Tub Appliques" available from Bath Innovations includes a vinyl tub appliques with suction cups. Another possible connecting device is a "soap Gripper" available from Selix of Chicago Ill. Finally, a particular adhesive believed useful to attach the connecting device to the structural base is a glue available from Bostik, #1142M.

It is possible to provide additive ingredients on the outer surface of the footcare device, such as for example mint, fragrance, kelp, sea salt, epsom salt, backing soda, alum, eucalyptus, hurps, moisturizer, beeswax, or mineral salts/potassium alum. These additives could be used to provide a body deodorant, different smells, different fragrances, etc. The additives could be in capsulated within the surface, applied by the user to the surface or other ways so that when the user rubes the foot over the abrasive surface it interacts with the additive that provide the scent or moisturizing quality that may be helpful in using the device.

It has been determined that the one important feature of the foot care device with the present application is that it provides a hands-free, stable base that when secured to a solid surface, such as a shower floor or tub, for a user to safely stand and rub his or her foot on the various cushions of the device to remove excess skin from the foot.

The device could be used in the bathroom in the shower or anywhere where a solid surface is available and for the user to rub one foot at a time on the device while the device remains in a stationary position, despite the pressure being applied thereto.

While the devices and methods described herein constitute preferred embodiments of the invention, it is to be understood that the invention is not limited to these precise devices and methods and that changes may be made therein without departing from the scope of the invention which is defined in the appended claims.

What is claimed is:

1. A device for at least partially alleviating skin discomfort, the device comprising:

a base structure having an upper and a bottom surface;

sufficient connecting means, operatively connected to the bottom surface of the base structure, for removably connecting the base structure to a solid surface such that the base structure remains substantially stable and stationery relative to the solid surface during use; and abrasive means, operatively connected to the upper surface of the base structure, for removing skin from a human anatomy.

2. The device of claim 1 further comprising:

abrasive means, operatively connected to the base structure, for removing skin build up from between the toes of a human foot.

3. The device of claim 2 wherein, the abrasive means comprises:

an elongated structure, operatively removably connected to the base structure.

4. The device of claim 2 wherein, the abrasive means comprises:

abrasive means, integral with the base structure.

5. The device of claim 1 wherein the base structure further comprises:

anyone of a plurality of abrasive materials.

6. The device of claim 5 wherein the abrasive material is selected from the group comprising:

concrete, silica, glass stone, ground pumice, volcanic rock, sand or Styrofoam.

7. The device of claim 1 wherein the connecting means further comprises:

at least four suction cups; and a plurality of gripper fingers.

8. The device of claim 1 wherein the connecting means further comprises:

at least four suction cups, operatively positioned on the base structure, such that a hands-free, stable base is provided when the at least four suction cups are secured to the solid surface.

9. The device of claim 8 wherein the at least four suction cups are about one-half inch in diameter.

10. The device of claim 8 wherein the at least four suction cups are from about three quarters of an inch to about two inches in diameter.

11. The device of claim 8 wherein the at least four suction cups are individual suction cups each individually operatively connected to the bottom of the base structure individually using an adhesive.

12. The device of claim 1 wherein the connecting means comprises:

a grip liner.

13. The device of claim 12 wherein the grip liner is operatively connected to the bottom of the base structure by an adhesive.

14. The device of claim 1 wherein additive ingredients are operatively positioned on the outer surface of the base structure.

15. A method for removing skin from a human anatomy, the method comprising the steps of:

providing a device for at least partially alleviating skin discomfort, the device including: a base structure having an upper and a bottom surface; sufficient connecting means, operatively connected to the bottom surface of the base structure, for removably connecting the base structure to a solid surface; and abrasive means, operatively connected to the upper surface of the base structure such that the base structure remains substantially stable and stationery relative to the solid surface during use, for removing skin from the human anatomy;

operatively positioning the device at a desired location on a flat, solid surface; and applying pressure from a point on top of the device to activate the connecting feature of the device, thereby securing the device in the desired location.

16. The method of claim 15 further comprising the step of:

wet and lather a foot with a thin layer of lubriant so that the foot can glide easily over the abrasive means.

17. The method of claim 16 further comprising the step of:

moving the foot over the upper surface of the device in at least one of a plurality of possible motions while applying slight pressure with the foot.

18. The method of claim 17 further comprising the step of:

operatively connecting a toe stick to the base structure; and guiding the contoured abrasive section of the contoured abrasive toe stick in between the desired toes to be rubbed.

19. The method of claim 18 further comprising the steps of:

positioning the toe stick between two toes;

gripping the toes to apply positive pressure to the abrasive toe stick with the toes; and rubbing the toes in an upward and downward motion.

20. The method of claim 19 further comprising the step of:

repeating the rubbing motion to maintain generally foot wellness and eliminate the build-up of calluses and flaking skin.

* * * * *